US012690629B2

(12) United States Patent
Liu et al.

(10) Patent No.: US 12,690,629 B2
(45) Date of Patent: Jul. 28, 2026

(54) NURSING GARMENT

(71) Applicant: Shenzhen Lute Jiacheng Supply Chain Management Co., Ltd., Shenzhen (CN)

(72) Inventors: Dong Liu, Shenzhen (CN); Lan Li, Shenzhen (CN)

(73) Assignee: Shenzhen Lute Jiacheng Supply Chain Management Co., Ltd., Shenzhen (CN)

( * ) Notice: Subject to any disclaimer, the term of this patent is extended or adjusted under 35 U.S.C. 154(b) by 0 days.

(21) Appl. No.: 19/064,869

(22) Filed: Feb. 27, 2025

(65) Prior Publication Data

US 2026/0206880 A1     Jul. 23, 2026

(30) Foreign Application Priority Data

Jan. 22, 2025   (CN) .......................... 202520159965.9

(51) Int. Cl.
A41C 3/04          (2006.01)
A61M 1/06          (2006.01)

(52) U.S. Cl.
CPC .............. A41C 3/04 (2013.01); A61M 1/062 (2014.02); A61M 2209/088 (2013.01)

(58) Field of Classification Search
CPC ........... A41C 3/04; A41C 3/08; A41C 3/0064; A41D 1/215

USPC .......................................................... 450/36
See application file for complete search history.

(56) References Cited

U.S. PATENT DOCUMENTS

| | | | | |
|---|---|---|---|---|
| 2,632,168 A | * | 3/1953 | Kaufman | ............. A41C 3/0021 |
| | | | | 450/87 |
| 2,738,509 A | * | 3/1956 | Bauder | ................... A41F 1/006 |
| | | | | 2/325 |
| 10,905,173 B1 | * | 2/2021 | Kosak | ................... A41F 15/002 |
| 11,641,889 B2 | * | 5/2023 | Eldreth | .................... A41C 3/02 |
| | | | | 450/1 |
| 12,161,173 B2 | * | 12/2024 | Zhang | ...................... A41C 3/04 |
| 2013/0109276 A1 | * | 5/2013 | Sporn | ...................... A41C 3/10 |
| | | | | 450/57 |
| 2023/0329359 A1 | * | 10/2023 | Akerson | ............. A41C 3/0014 |

* cited by examiner

*Primary Examiner* — Timothy K Trieu

(57) ABSTRACT

The present application discloses a nursing garment comprising: a shoulder strap, wherein a first connecting structure is provided on the shoulder strap; a first layer, wherein a second connecting structure is provided on the first layer; a second layer, wherein a third connecting structure and a perforation are provided on the second layer, the perforation being configured to allow the second connecting structure to pass through and detachably connect with the third connecting structure; the second layer further comprises a fourth connecting structure, which is configured to detachably connect with the first connecting structure, such that allowing the first layer and the second layers to be detached from the shoulder strap together, thereby at least partially exposing the wearer's breast.

16 Claims, 5 Drawing Sheets

NURSING GARMENT

CROSS-REFERENCE TO RELATED APPLICATIONS

The present application claims priority to Chinese Patent Application No. 202520159965.9, filed on Jan. 22, 2025, the entire contents of which are incorporated herein by reference.

TECHNICAL FIELD

The present application relates to the technical field of maternal and baby products, particularly to a nursing garment.

BACKGROUND

When using a breast pump, the mother must manually position the breast flange or breast shield over the exposed portion of the breast. Since the time required for milk expression using a breast pump is relatively long, mothers typically express milk from both breasts at the same time. In order to express milk from both breasts, the mother must hold the breast flanges or shields with both hands, which places her in an awkward position and makes it difficult to perform even simple tasks, such as operating the breast pump. As a result, breastfeeding women are unable to fully utilize their hands to complete other tasks. Therefore, developing a device that allows the mother to use the breast pump while also enabling her to use her hands freely for other tasks would be highly beneficial.

Hands-free breast pumps allow the mother to simultaneously massage her breasts to promote milk flow, a feature that most breast pumps currently in use are unable to offer, or they allow the mother to engage in other work while pumping. To address the disadvantages of having to manually hold the breast pump during milk expression, a supporting breast pump or breastfeeding garment is typically designed with at least two layers, with an opening in the inner layer to form a passage for breastfeeding or for inserting the breast pump. The outer layer covers the inner layer during normal wear to ensure privacy.

Traditional nursing garments suffer from issues such as inconvenient disassembly or uncomfortable wear. When designing small-sized connecting clasps, interference between several clasps may occur, causing discomfort when the clasps press against the wearer's body. Additionally, the inner and outer layers do not connect or detach smoothly, particularly when the clasps on the shoulder straps are simultaneously connected to the clasps on both the inner and outer layers. The clasps tend to pile up, making it difficult to disassemble the garment and reducing comfort.

SUMMARY

In view of the shortcomings of the prior art, this application provides a nursing garment designed to address issues with unsmooth detachment and connection.

In order to solve the above technical problem, one embodiment of this application proposes a nursing garment comprising: a shoulder strap, wherein a first connecting structure is provided on the shoulder strap; a first layer, wherein a second connecting structure is provided on the first layer; a second layer, wherein a third connecting structure and a perforation are provided on the second layer, the perforation being configured to allow the second connecting structure to pass through and detachably connect with the third connecting structure; the second layer further comprises a fourth connecting structure, which is configured to detachably connect with the first connecting structure, such that allowing the first layer and the second layer to be detached from the shoulder strap together, thereby at least partially exposing the wearer's breast.

In one embodiment, the shoulder strap further comprises a fifth connecting structure, which is configured to detachably connect with the second connecting structure, so that the second connecting structure can detach from the third connecting structure and, after being withdrawn from the perforation, can connect with the fifth connecting structure.

In one embodiment, the first layer comprises an opening, the opening being configured to support at least a portion of a breast pump inserted into the opening, or the opening being configured to allow the user's nipple to protrude through the opening for breastfeeding.

In one embodiment, the first layer is positioned closer to the wearer than the second layer when the nursing garment is worn.

In one embodiment, the second layer is positioned closer to the wearer than the first layer when the nursing garment is worn.

In one embodiment, the edge of the perforation is reinforced with a reinforcement strip, the reinforcement strip being attached to the second layer by an adhesive film.

In one embodiment, wherein the edge of the perforation is reinforced with a reinforcement strip, the reinforcement strip being sewn to the edge of the perforation on the second layer.

In one embodiment, wherein one of the first connecting structure and the fourth connecting structure is a hook structure, and the other is a loop structure, groove structure, or hole structure.

In one embodiment, wherein one of the second connecting structure and the third connecting structure is a hook structure, and the other is a loop structure, groove structure, or hole structure.

In one embodiment, wherein the first connecting structure is a first clasp, the first clasp having a first hook, the fourth connecting structure is a second clasp, the second clasp having a slot.

In one embodiment, wherein the third connecting structure is a loop, the second connecting structure is a third clasp, and the third clasp has a second hook.

In one embodiment, wherein the opening is formed between three edges of the first layer, the three edges at least partially overlapping.

In one embodiment, wherein the elasticity of the three edges is greater than the elasticity of other portions of the first layer.

In one embodiment, wherein any two of the three edges are not parallel to each other.

In one embodiment, wherein the loop is a sewn loop attached to the second layer, the sewn loop being formed by sewing the ends of a fabric strip to the second layer.

In one embodiment, wherein the loop is formed by attaching the ends of a fabric strip to the second layer.

In one embodiment, wherein the first layer and the second layer are made of different types of fabric.

In one embodiment, wherein the opening is a slit formed on the first layer.

In one embodiment, wherein the first layer and the second layer are made of the same fabric.

In one embodiment, wherein the second connecting structure is located at the upper end of the first layer, and the third connecting structure is located at the upper end of the second layer.

The embodiment of this application provides a nursing garment comprising: a shoulder strap, wherein a first connecting structure is provided on the shoulder strap; a first layer, wherein a second connecting structure is provided on the first layer; a second layer, wherein a third connecting structure and a perforation are provided on the second layer, the perforation being configured to allow the second connecting structure to pass through and detachably connect with the third connecting structure; the second layer further comprises a fourth connecting structure, which is configured to detachably connect with the first connecting structure, such that allowing the first layer and second layer to be detached from the shoulder strap together, thereby at least partially exposing the wearer's breast. This arrangement ensures smooth disassembly and connection of the layers of the nursing garment and improves the comfort of wear.

BRIEF DESCRIPTION OF THE DRAWINGS

To further clarify the technical solutions in the embodiments of this application or the prior art, a brief introduction to the drawings that need to be used in the description of the embodiments or prior art will be provided below. It is obvious that the drawings described below are merely some embodiments of this application, and for those skilled in the art, additional drawings may be obtained based on the structures shown in these drawings without requiring inventive effort.

Figure 1:
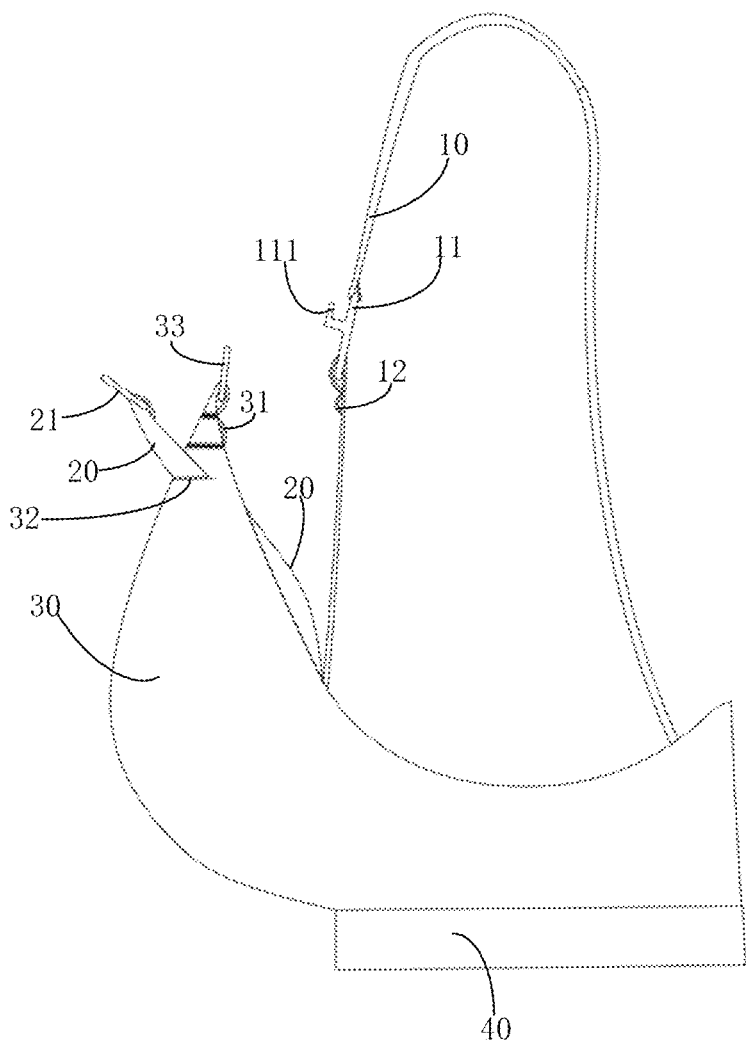
FIG. 1 is a schematic side view of the nursing garment in one embodiment of this application, with the first and second layers detached from the shoulder strap and the first layer passing through the second layer.

The realization, functional characteristics, and advantages of the objectives of this application will be further explained in combination with the embodiments, with reference to the drawings.

DETAILED DESCRIPTION OF THE EMBODIMENTS

In this application, the terms "provided," "disposed," and "connected" should be broadly understood. For example, they can refer to fixed connections, detachable connections, or integrated structures. They may indicate mechanical connections or electrical connections, direct connections, or indirect connections through an intermediary, or they may refer to internal communication between two devices, components, or parts. A person skilled in the art can understand the specific meaning of these terms in this application according to the context.

The terms "center," "longitudinal," "transverse," "length," "width," "thickness," "top," "bottom," "front," "back," "left," "right," "vertical," "horizontal," "inner," "outer," "radial," and "circumferential" indicate directional or positional relationships based on the orientation or positional relationships shown in the figures. These terms are used solely to simplify and clarify the description of the present application and should not be interpreted as limiting the invention to a specific orientation, construction, or operation.

Additionally, the terms "first" and "second" are used only for descriptive purposes and should not be understood as indicating relative importance or implying the number of features. Therefore, a "first" or "second" feature may explicitly or implicitly include one or more of that feature. In the description of this application, "multiple" means at least two, such as two or three, unless otherwise explicitly specified.

Moreover, the above terms, in addition to indicating directional or positional relationships, may also have other meanings. For example, the term "top" may also refer to attachment or connection relationships. A person skilled in the art can understand these terms according to the specific context.

Breastfeeding offers numerous benefits for both infants and nursing women. Breast milk contains all the essential nutrients needed for an infant's growth and development. Breastfed infants tend to be healthier, with fewer incidences of middle ear infections and respiratory tract infections, and they have a lower risk of allergies, cancer, childhood diabetes, and obesity. They are also less prone to heart disease, eczema, and asthma. For breastfeeding women, it can reduce the chances of postpartum bleeding and anemia, aid in uterine recovery, and help burn an additional 500 calories per day.

However, due to work schedules and other time demands, not all nursing women can feed their babies on demand. Consequently, many use breast pumps to extract and store breast milk for feeding. A breast pump system typically includes a breast shield, a funnel-shaped device with a conical area that fits against the breast with the nipple centered in the shield. When negative pressure is applied, the nipple is drawn into the shield's tubular section, usually into the nipple channel. The nipple channel connects to other components of the breast milk collection kit, allowing periodic negative pressure to be applied inside the breast shield. This connection also provides a flow path for the expressed milk, enabling its collection in a container. The container can be a breast milk bottle with a screw cap, which can later be used as a baby feeding bottle. Nursing women often need to hold the breast shield in place to express milk.

It is foreseeable that securing the breast shield by hand is inconvenient and restricts what tasks women can perform during pumping. Although various bras and nursing garments have been developed to hold the breast shield, they generally do not secure it well, requiring adjustments or repositioning.

Figure 2:
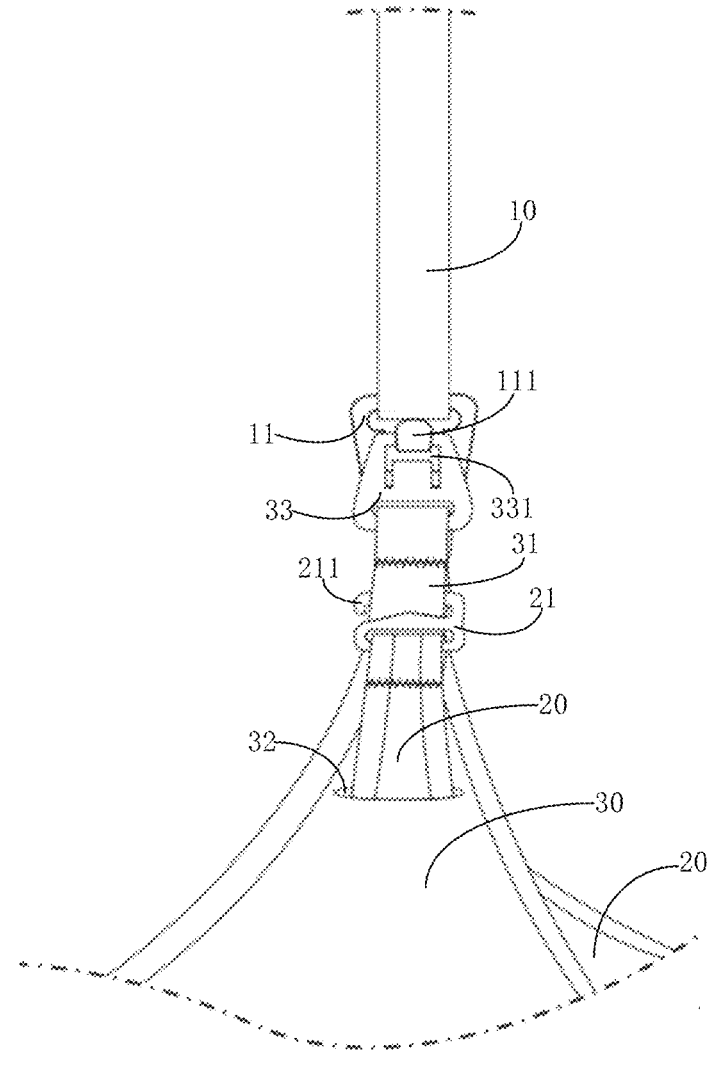
FIG. 2 is a schematic view of a partial structure of the nursing garment in one embodiment of this application in its normal wearing state.
Figure 3:
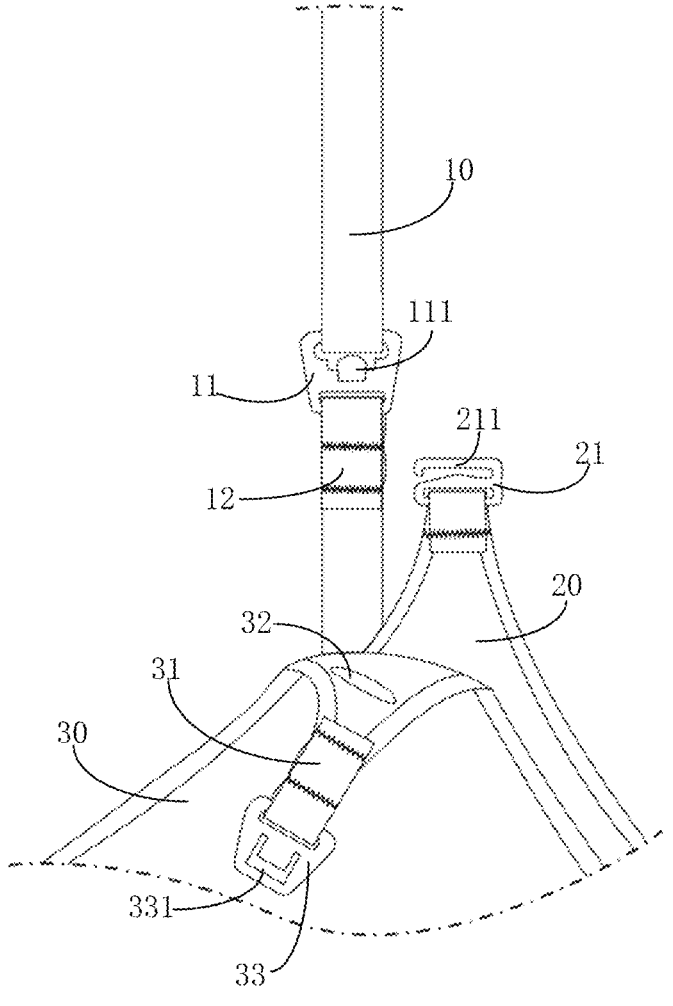
FIG. 3 is a schematic view of a partial structure of the nursing garment in one embodiment of this application in the state where the layers are detached.
Figure 4:
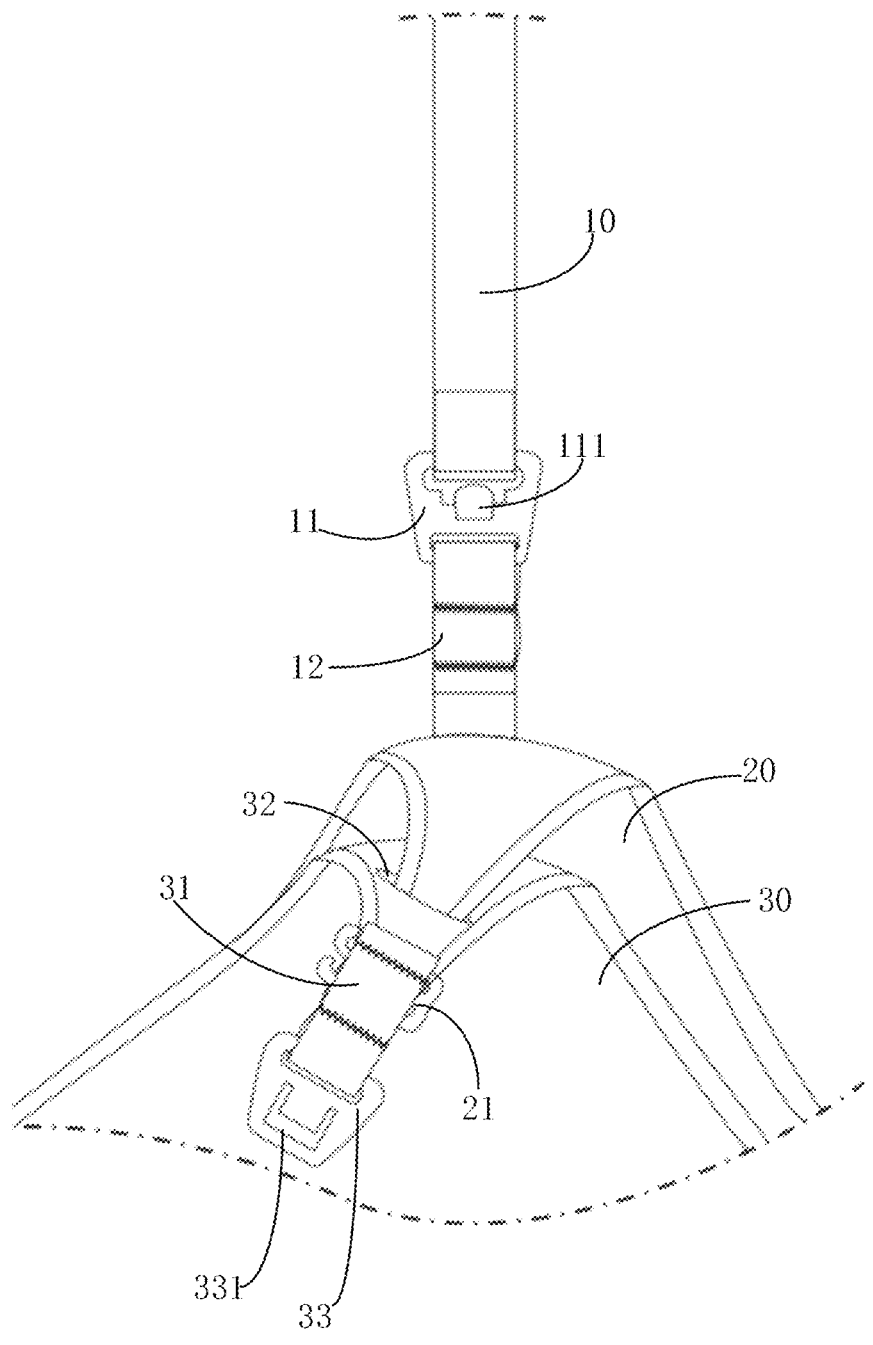
FIG. 4 is a schematic view of a partial structure of the nursing garment in one embodiment of this application in the state where both the first and second layers are detached from the shoulder strap.
Figure 5:
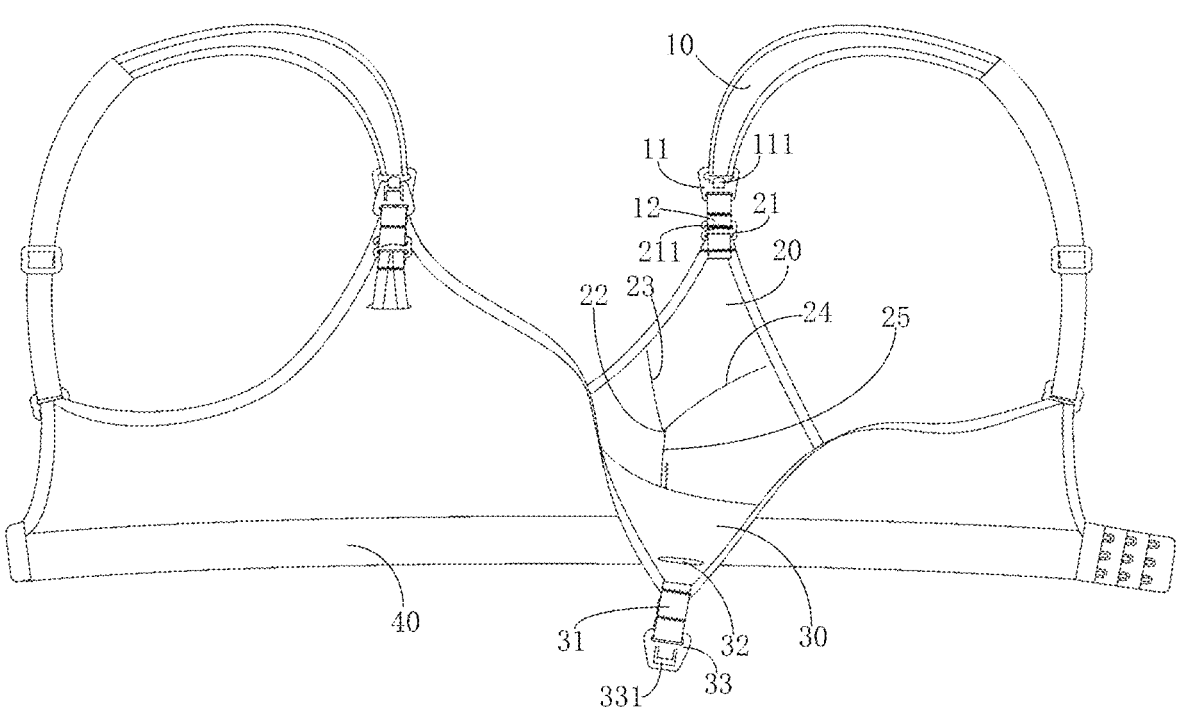
FIG. 5 is a schematic front view of the nursing garment in one embodiment of this application, with the first layer connected to the shoulder strap and the second layer detached from the shoulder strap.
Figure 6:
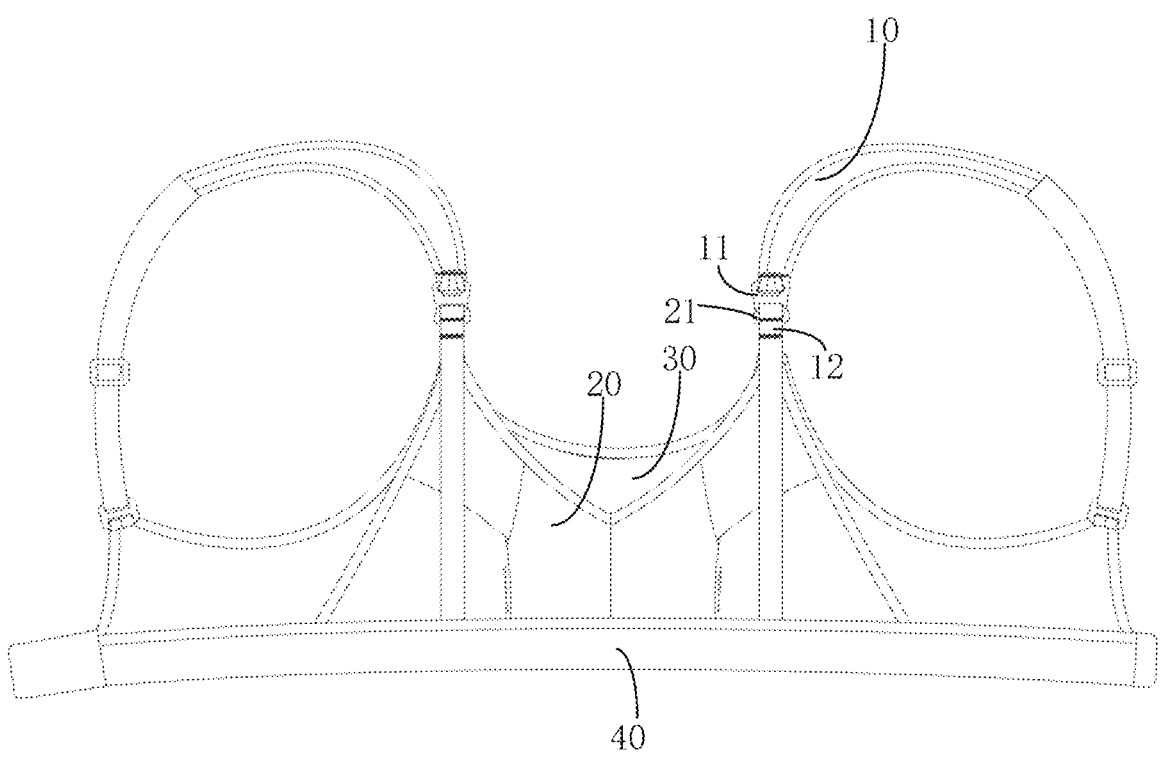
FIG. 6 is a schematic rear view of the nursing garment in one embodiment of this application.

Please refer to FIG. 1 to FIG. 6. FIG. 1 is a schematic side view of the nursing garment in one embodiment of this application, with the first and second layers detached from the shoulder strap and the first layer passing through the second layer. FIG. 2 is a schematic view of a partial structure of the nursing garment in one embodiment of this application in its normal wearing state. FIG. 3 is a schematic view of a partial structure of the nursing garment in one embodiment of this application in the state where the layers are detached. FIG. 4 is a schematic view of a partial structure of the nursing garment in one embodiment of this application in the state where both the first and second layers are detached from the shoulder strap. FIG. 5 is a schematic front view of the nursing garment in one embodiment of this application, with the first layer connected to the shoulder strap and the second layer detached from the shoulder strap. FIG. 6 is a schematic rear view of the nursing garment in one embodiment of this application.

In the embodiments of this application, the nursing garment is described using a bra as an example. The nursing garment of this embodiment includes a shoulder strap 10, a first layer 20, and a second layer 30.

As shown in FIG. 1, FIG. 5, and FIG. 6, in some embodiments, the nursing garment may also include a lower bust band 40, which is arranged to encircle the wearer's torso when worn. The lower ends of the first layer 20 and the second layer 30 are connected to the lower bust band 40. Both the first layer 20 and the second layer 30 can rotate relative to the lower bust band 40.

As shown in FIG. 1 to FIG. 6, the shoulder strap 10 is provided with a first connecting structure 11. The first layer 20 is provided with a second connecting structure 21. The second layer 30 is provided with a third connecting structure 31 and a perforation 32, wherein the perforation 32 is configured to allow the second connecting structure 21 to pass through the perforation 32 and detachably connect with the third connecting structure 31. The second layer 30 is also provided with a fourth connecting structure 33, which is configured to detachably connect with the first connecting structure 11, such that allowing the first layer 20 and the second layer 0 to be detached from the shoulder strap 10 together, thereby at least partially exposing the wearer's breast. As shown in FIG. 1 to FIG. 6, in one embodiment, the first connecting structure 11 may be arranged in series on the shoulder strap 10, meaning that the two ends of the first connecting structure 11 are connected to different positions on the shoulder strap 10. In other embodiments, the first connecting structure 11 may be connected to the shoulder strap 10 at only one end, and this embodiment is not limited by this particular arrangement.

In one embodiment, the second connecting structure 21 may be located at the upper end of the first layer 20, and the third connecting structure 31 may be located at the upper end of the second layer 30. In other embodiments, the second connecting structure 21 may be located at another position on the first layer 20, such as a position slightly above the center. Similarly, the third connecting structure 31 may be located at another position on the second layer 30, such as a position slightly above the center. This embodiment is not limited by these specific arrangements.

As shown in FIG. 3 and FIG. 5, in one embodiment, the shoulder strap 10 is also provided with a fifth connecting structure 12, which is configured to detachably connect with the second connecting structure 21. This enables the second connecting structure 21 to be detached from the third connecting structure 31 and pulled out from the perforation 32, after which it can be connected to the fifth connecting structure 12. The second connecting structure 21 is selectively detachably connected with either the fifth connecting structure 12 or the third connecting structure 31, with different connection states adapting to different usage scenarios.

As shown in FIG. 5, in one embodiment, the first layer 20 is provided with an opening 22, which is configured to support at least a portion of a breast pump inserted into the opening 22 or allow the user's nipple to protrude through the opening 22 for breastfeeding. In one embodiment, the opening 22 is formed between three edges 23, 24, and 25 of the first layer 20, the three edges at least partially overlapping. The opening 22 in this embodiment is suitable for supporting a breast pump, providing stable support through these three edges 23, 24, and 25. These three edges are located on the inner side of the first layer 20 rather than the outer side. Any two of the three edges 23, 24, and 25 are not parallel to each other.

In one embodiment, the elasticity of the three edges 23, 24, and 25 is greater than that of other portions of the first layer 20. By setting the elasticity of the three edges larger than other areas, it can contract when supporting a breast pump, thus achieving stable support. In some embodiments, the three edges 23, 24, and 25 may be reinforced by applying one or multiple layers of reinforcement strips through a bonding process, wherein the intermediate adhesive film used in the bonding process is elastic.

In some embodiments, the opening could also be a slit. In such embodiments, the slit allows the wearer's breast or part of the breast (e.g., the nipple) to pass through for breastfeeding. It should be understood that the shape and structure of the opening are not limited to the ways described in the embodiments of this application, as long as it can support a breast pump or allow the nipple to protrude for breastfeeding.

In one embodiment, the first layer 20 is positioned closer to the wearer than the second layer 30 when the nursing garment is worn. In other embodiments, the second layer 30 may be positioned closer to the wearer than the first layer 20 when the nursing garment is worn.

In one embodiment, the first layer 20 and the second layer 30 may be made of the same type of fabric. In other embodiments, the first layer 20 and the second layer 30 may be made of different types of fabric. For example, the first layer 20 may be made of a more skin-friendly fabric, while the second layer 30 may be made of waterproof, wear-resistant, or other types of fabric; the embodiments of this application do not limit this aspect.

In one embodiment, the edge of the perforation 32 is reinforced with a reinforcement strip (not shown), which is attached to the second layer 30 by an adhesive film. In another embodiment, the edge of the perforation is reinforced with a reinforcement strip sewn to the edge of the perforation on the second layer 30. The reinforcement strip prevents the edge of the perforation 32 from wrinkling or tearing, especially after prolonged washing.

In one embodiment, one of the first connecting structure 11 and the fourth connecting structure 33 is a hook structure, and the other is a loop structure, groove structure, or hole structure. Similarly, one of the second connecting structure 21 and the third connecting structure 31 is a hook structure, and the other is a loop structure, groove structure, or hole structure.

In other embodiments, one of the first connecting structure and the fourth connecting structure could be the hook side of Velcro, and the other could be the loop side of Velcro. Similarly, one of the second connecting structure and the third connecting structure could be the hook side of Velcro, and the other could be the loop side of Velcro.

In other embodiments, the first connecting structure and the fourth connecting structure may adopt other detachable connection structures, and the embodiments of this application do not limit this aspect. Similarly, the second connecting structure and the third connecting structure may use other detachable connection structures, and the embodiments of this application do not limit this aspect.

In one embodiment, the first connecting structure 11 is a first clasp 11, equipped with a first hook 111, and the fourth connecting structure 33 is a second clasp 33, equipped with a slot 331. The first hook 111 and the slot 331 match to achieve a detachable connection between the first connecting structure 11 and the fourth connecting structure 33. The slot 331 is roughly U-shaped, forming a spring-like structure inside the slot 331 to ensure there is some elastic space when the first hook 111 connects with the slot 331, improving the smoothness of connection and disconnection.

In one embodiment, the third connecting structure 31 is a loop 31, and the second connecting structure 21 is a third clasp 21, equipped with a second hook 211. In one embodiment, the loop 31 can be a sewn loop formed by sewing both ends of a fabric strip to the second layer 30, or it can be a loop formed by attaching both ends of a fabric strip to the first layer 20; the embodiments of this application do not limit this aspect.

In this embodiment, the fifth connecting structure 12 and the first connecting structure 11 are different structures located at different positions, with the first connecting structure 11 being a hook and the fifth connecting structure 12 being a loop 12. It should be understood that in other embodiments, the fifth connecting structure and the first connecting structure can be the same structure, meaning that the function of the fifth connecting structure can be achieved by using the first connecting structure alone. That is, the second connecting structure 21 selectively detachably connects with either the first connecting structure 11 or the third connecting structure 31. After the second connecting structure 21 detaches from the third connecting structure 31 and is withdrawn from the perforation 32, it can connect with the first connecting structure 11, thereby supporting the first layer 20 and, consequently, supporting at least a portion of a breast pump inserted into the opening 22 or allowing the user's nipple to protrude through the opening 22 for breastfeeding.

The following section describes the usage scenarios of the nursing garment, based on the embodiments of this application, with reference to the accompanying drawings.

As shown in FIG. 2, in one usage scenario, after the second connecting structure 21 passes through the perforation 32, it connects with the third connecting structure 31; simultaneously, the fourth connecting structure 33 connects with the first connecting structure 11. In this connected state, the nursing garment is used for normal wear, where both the first layer 20 and the second layer 30 are in a covered state, protecting the wearer's privacy during daily work and life.

As shown in FIG. 5, in another usage scenario, the fourth connecting structure 33 detaches from the first connecting structure 11 on the shoulder strap 11, the second layer 30 is flipped outward to open, the second connecting structure 21 detaches from the third connecting structure 31, and after being withdrawn from the perforation 32, the second connecting structure 21 then connects to the fifth connecting structure 12. This connection setup allows the nursing garment to be used for supporting a breast pump through the opening 22 on the first layer 20 or for breastfeeding through the opening 22.

As shown in FIG. 4, in yet another usage scenario, after the second connecting structure 21 passes through the perforation 32, it connects with the third connecting structure 31; meanwhile, the fourth connecting structure 33 detaches from the first connecting structure 11. The first layer 20 and the second layer 30 are both flipped outward to open. In this configuration, the nursing garment fully exposes the wearer's breast for breastfeeding.

The embodiments of this application provide a nursing garment that includes: shoulder straps, wherein the shoulder straps are equipped with a first connecting structure; a first layer, wherein the first layer is provided with a second connecting structure; a second layer, wherein the second layer is provided with a third connecting structure and a perforation configured to allow the second connecting structure to pass through the perforation and detachably connect with the third connecting structure; additionally, the second layer is also provided with a fourth connecting structure which is configured to detachably connect with the first connecting structure so as to enable the first layer and the second layer to be jointly detached from the shoulder straps, thereby at least partially exposing the wearer's breasts. This design ensures smooth detachment and connection of various layers of the nursing garment and enhances wearing comfort.

While certain features of the embodiments of the subject matter claimed have been illustrated and described herein, many modifications, substitutions, changes, and equivalents will now occur to those skilled in the art. Moreover, although several functional modules and their relationships have been described in detail, it is believed by those skilled in the art that some operations can be performed without using other functional modules, or other functions or relationships between functions can be established while still conforming to the subject matter claimed. Therefore, it is intended that the appended claims encompass all such modifications and variations that fall within the true spirit and scope of the embodiments of the claimed subject matter.

The above description only provides specific embodiments of the present application. It should be noted that for ordinary technicians in the technical field, without departing from the principles of the present application, several improvements and embellishments can also be made, which should also be regarded as falling within the protection scope of the present application.

What is claimed is:

1. A nursing garment, comprising:

a shoulder strap, wherein a first connecting structure is provided on the shoulder strap;

a first layer, wherein a second connecting structure is provided on the first layer; the first layer comprises an opening, the opening being configured to support at least a portion of a breast pump inserted into the opening, or the opening being configured to allow the user's nipple to protrude through the opening for breastfeeding;

a second layer, wherein a third connecting structure and a perforation are provided on the second layer, the perforation being configured to allow the second connecting structure to pass through and detachably connect with the third connecting structure; the second layer further comprises a fourth connecting structure, which is configured to detachably connect with the first connecting structure, such that allowing the first layer and the second layer to be detached from the shoulder strap together, thereby when the garment is worn and when the outer layer and the inner layer are detached from the shoulder strap together, the wearer's breast is at least partially exposed.

2. The nursing garment of claim 1, wherein the shoulder strap further comprises a fifth connecting structure, which is configured to detachably connect with the second connecting structure, so that the second connecting structure can detach from the third connecting structure and, after being withdrawn from the perforation, can connect with the fifth connecting structure.

3. The nursing garment of claim 1, wherein the first layer is positioned closer to the wearer than the second layer when the nursing garment is worn.

4. The nursing garment of claim 1, wherein the second layer is positioned closer to the wearer than the first layer when the nursing garment is worn.

5. The nursing garment of claim 1, wherein an edge of the perforation is reinforced with a reinforcement strip, the reinforcement strip being attached to the second layer by an adhesive film.

6. The nursing garment of claim 1, wherein the edge of the perforation is reinforced with a reinforcement strip, the reinforcement strip being sewn to the edge of the perforation on the second layer.

7. The nursing garment of claim 1, wherein one of the first connecting structure and the fourth connecting structure is a hook structure, and the other is a loop structure, groove structure, or hole structure.

8. The nursing garment of claim 7, wherein the first connecting structure is a first clasp, the first clasp having a first hook, the fourth connecting structure is a second clasp, the second clasp having a slot.

9. The nursing garment of claim 7, wherein the third connecting structure is a loop, the second connecting structure is a third clasp, and the third clasp has a second hook.

10. The nursing garment of claim 7, wherein the loop is a sewn loop attached to the second layer, the sewn loop being formed by sewing the ends of a fabric strip to the second layer.

11. The nursing garment of claim 7, wherein the loop is formed by attaching the ends of a fabric strip to the second layer.

12. The nursing garment of claim 1, wherein one of the second connecting structure and the third connecting structure is a hook structure, and the other is a loop structure, groove structure, or hole structure.

13. The nursing garment of claim 1, wherein the first layer and the second layer are made of different types of fabric.

14. The nursing garment of claim 1, wherein the opening is a slit formed on the first layer.

15. The nursing garment of claim 1, wherein the first layer and the second layer are made of the same fabric.

16. The nursing garment of claim 1, wherein the second connecting structure is located at the upper end of the first layer, and the third connecting structure is located at the upper end of the second layer.

* * * * *